US010602753B2

(12) United States Patent
Giuseppin et al.

(10) Patent No.: US 10,602,753 B2
(45) Date of Patent: Mar. 31, 2020

(54) PRODUCTION OF YOGURT

(71) Applicant: Coöperatie AVEBE U.A., Veendam (NL)

(72) Inventors: Marco Luigi Federico Giuseppin, Veendam (NL); Robin Eric Jacobus Spelbrink, Veendam (NL); Catharina Maria Antoinette Mooij, Veendam (NL)

(73) Assignee: Coöperatie AVEBE U.A., Veendam (NL)

( * ) Notice: Subject to any disclaimer, the term of this patent is extended or adjusted under 35 U.S.C. 154(b) by 0 days.

(21) Appl. No.: 15/309,372

(22) PCT Filed: May 8, 2015

(86) PCT No.: PCT/NL2015/050324
§ 371 (c)(1),
(2) Date: Nov. 7, 2016

(87) PCT Pub. No.: WO2015/170985
PCT Pub. Date: Nov. 12, 2015

(65) Prior Publication Data
US 2017/0055541 A1 Mar. 2, 2017

(30) Foreign Application Priority Data
May 9, 2014 (EP) .................................. 14167734

(51) Int. Cl.
A23C 9/133 (2006.01)
A23C 9/13 (2006.01)
(52) U.S. Cl.
CPC .................. A23C 9/1315 (2013.01)
(58) Field of Classification Search
CPC .................................................. A23C 9/1315
(Continued)

(56) References Cited

U.S. PATENT DOCUMENTS

| 3,932,680 A | * | 1/1976 | Egli | ........................ | A23C 9/133 |
| | | | | | 426/34 |
| 2012/0021093 A1 | * | 1/2012 | Qvist | ................... | A23C 9/1209 |
| | | | | | 426/43 |
| 2013/0066048 A1 | * | 3/2013 | Raskin | ................... | A61K 36/48 |
| | | | | | 530/350 |

FOREIGN PATENT DOCUMENTS

| EP | 1920662 A1 | 5/2008 |
| EP | 2191731 A1 | 6/2010 |

(Continued)

OTHER PUBLICATIONS

Pots, André M., et al. "The effect of storage of whole potatoes of three cultivars on the patatin and protease inhibitor content; a study using capillary electrophoresis and MALDI-TOF mass spectrometry." Journal of the Science of Food and Agriculture 79.12 (1999): 1557-1564.

(Continued)

Primary Examiner — Jeffrey P Mornhinweg
(74) Attorney, Agent, or Firm — Hoffmann & Baron, LLP

(57) ABSTRACT

The present invention is in the field of fermentation, and pertains to a method for preparing yogurt by fermentation, comprising the steps of providing a fermentation starter culture comprising a selected microorganism in a suitable culture medium, adding a potato protein protease inhibitor to the culture medium, culturing the microorganism, and harvesting the yogurt. This method has the advantage that the lag time of fermentation can be reduced by the addition of relatively low amounts of potato protein protease inhibitor. It has the additional advantage that the potato protein protease inhibitor allows for application of the present method over a wide pH range and wide temperature range including pasteurization, is filter sterilizable and that potato protease inhibitor protein is non-allergenic.

2 Claims, 6 Drawing Sheets

(58) Field of Classification Search
USPC .......................................................... 426/43
See application file for complete search history.

(56) References Cited

FOREIGN PATENT DOCUMENTS

| | | |
|---|---|---|
| WO | 2008069650 A1 | 6/2008 |
| WO | 2009061186 A1 | 5/2009 |

OTHER PUBLICATIONS

Spelbrink, Robin EJ, et al. "Quantitative determination of trypsin inhibitory activity in complex matrices." Open Food Science Journal 5 (2011): 42-46.
"Animal feeding stuffs—Determination of trypsin inhibitor activity of soya products". 1st edition Oct. 15, 2001, ISO 14902:2001(E).
Speransky, Anna S., et al. "Kunitz-type protease inhibitors group B from Solanum palustre." Biotechnology journal 2.11 (2007): 1417-1424.
Tomoko Yoshimoto et al., "Properties of Soymilk and Yogurt-like Food prepared by using Defatted Soybean Flour," Nippon Shokuhin Kagaku Kogaku Kaishi, 2001, vol. 48, No. 12, pp. 906-912. (English Abstract, and English translation of item 3 on p. 907, and of paragraph bridging pp. 909-910.).
Tomoko Murakami et al., "Use of Soymilk for Yogurt," New Food Industry, 1997. vol. 39, No. 12, pp. 65-71. (English translation of p. 66, 4th paragraph, and of item 4 on pp. 68-69.).

\* cited by examiner

PRODUCTION OF YOGURT

This application is the U.S. National Phase of, and Applicants claim priority from, International Patent Application Number PCT/NL2015/050324 filed 8 May 2015, which claims priority from EP 14167734.4 filed 9 May 2014, each of which is incorporated herein by reference.

BACKGROUND OF THE INVENTION

The invention is in the field of yogurt production by fermentation. Fermentation is a well-known technique for the production of yogurt using the metabolic activity of microorganisms that release acid.

Microorganisms that release acid are well-known to be used in a feed culture comprising milk, resulting in yogurt that has a longer shelf-life than milk. Examples of well-known acid-releasing microorganisms for use in yogurt production are microorganisms from the genus: *Lactobacillus, Lactococcus* and *Streptococcus*.

In a typical yogurt fermentation process, three phases can be distinguished. The first phase starts when the microorganisms are combined with the fermentation feed, usually a milk-based feed. The microorganisms adapt to their new environment, and start to take up nutrients, such as peptides, amino acids, vitamins and minerals. In this phase, the microorganisms produce enzymes required for cell division and growth, for spending energy, and for making storage materials, building blocks or nutrients. In this phase, however, there is barely microorganism growth, or any other visual indication that anything is happening in the fermentation. For this reason, this phase is called the lag phase.

The lag phase is characterized in that the presence of certain nutrients may be the limiting factor for growth. An example is a system in which the amount of peptides is insufficient to allow for normal microorganism growth or a normal microorganism growth rate. As long as peptide presence remains insufficient, growth remains limited by the peptide concentration. Even though it appears nothing happens, this phase is very important for the fermentation process because the health of the population of microorganisms determines the quality of the resulting yogurt.

When the microorganisms have adapted to their environment, the second phase initiates. This phase, characterized by a non-substrate limited microorganism growth, is called the exponential phase. During the exponential phase, the microorganisms start to grow by cell division, and therefore multiply exponentially. In this phase, the microorganisms as a consequence of their metabolic character produce among others lactic acid.

At the end of the exponential phase, the amount of suitable nutrients has often decreased such that exponential growth can no longer be sustained by the fermenting milk mixture. Thus, growth slows down and the fermentation enters the stationary phase. In this phase, growth is no longer exponential, although cell division still occurs, and the fermenting mixture slowly attains an equilibrium between all present compounds. If all circumstances are appropriate, this results in a yogurt product of high quality, with well-balanced flavor and smell.

The time these stages require is highly variable, and dependent on the type of microorganism(s) used, the type of fermentation feed, the temperature and many other parameters. Given these distinct phases, production of yogurt is commonly a batch process. As is common for batch processes, an important factor in cost is the time required for the product to be ready.

An important factor in production time is the lag phase. During this phase, the actual fermentation process is prepared. Apart from creating the adequate conditions for microorganism growth, there is no contribution at all to the making of the product of interest, and as such, a shorter lag phase would have a huge impact on the economy of the fermentation process. However, the lag phase is very important for determining the health of the population of microorganisms, which in turn is important for the quality of the yogurt. The time that is required for the lag phase to pass and the fermentation process to reach the exponential phase is referred to as the lag time.

Attempts to reduce the lag time have been made before. One option is to use a semi-continuous fermentation process, in which the microorganisms are adapted to the production stage and remain in the exponential phase for a prolonged time. This however, is often not suitable, because the stationary phase is important for determining the final taste and/or quality of the yogurt, and this phase is bypassed in such a semi-continuous process.

Also, it is possible to a d a mix of microorganisms, called a starter culture, which have already been adapted to the medium conditions of the fermentation. This, however, creates different problems, because in a small-scale premix microorganism feed, the environment of the full-scale fermentor is difficult to copy. It is possible to use a larger volume of the preculture (inoculum), but this has a big impact on the production process and costs of the preculture stage. Therefore, it would be preferred to reduce the lag time, possibly even further than possible with this technique, in a reliable way, with a limited amount of starter culture.

For reducing the lag time, it is also possible to add extra easily transportable and energy beneficial nutrients to the premix, as for instance extra peptides. However, this creates additional costs and problems with for instance off-taste and coloring.

SUMMARY OF THE INVENTION

The present invention is related to a method for preparing yogurt by fermentation, comprising the steps of providing a fermentation starter culture comprising a selected microorganism in a suitable culture medium, adding a plant protein protease inhibitor to the culture medium, preferably a potato protein protease inhibitor, culturing the microorganism in the culture medium, and harvesting the yogurt.

It has been found that addition of potato protein protease inhibitor to a fermentation feed significantly reduces the lag time of the fermentation. The required amount of potato protein is low enough not to affect the taste the yogurt, and the lag time reduction occurs both in batch- and in semi-continuous processes.

DETAILED DESCRIPTION

Figure 1:
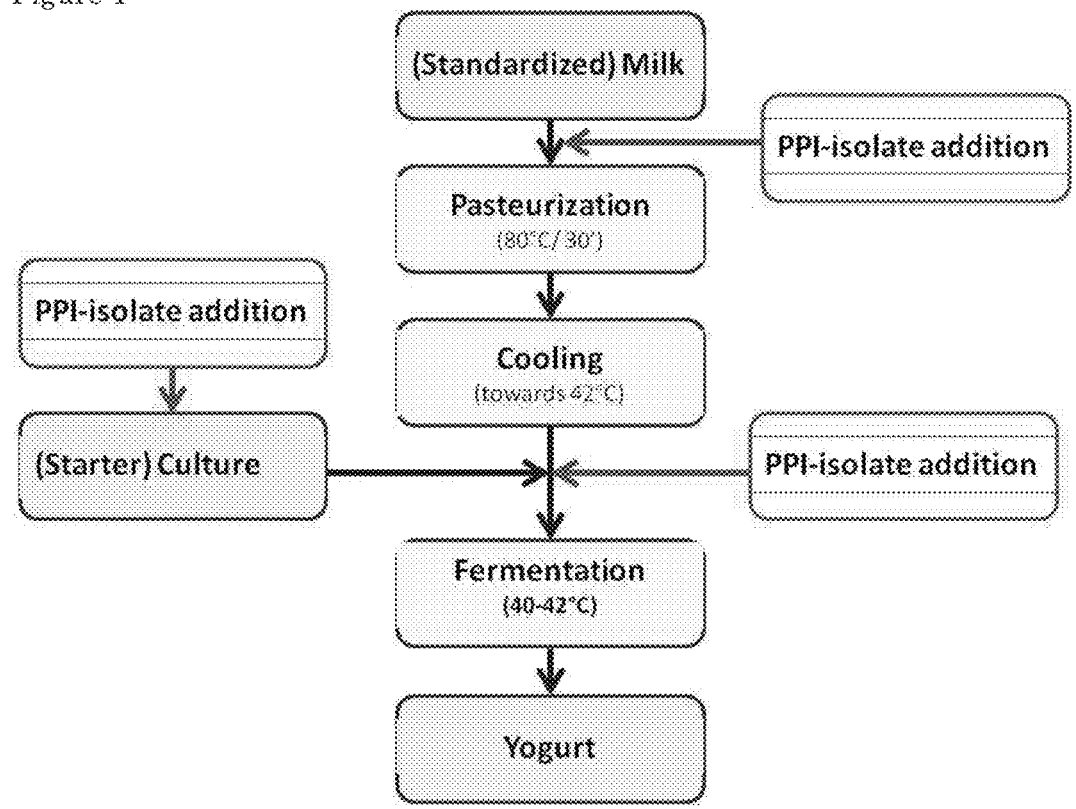
FIG. 1: flow scheme for yogurt production.

The present invention pertains to a method for preparing yogurt, comprising the steps of providing a fermentation starter culture comprising a selected microorganism in a suitable culture medium, adding a plant protein protease inhibitor to the culture medium, preferably a potato protein protease inhibitor, culturing the microorganism in the culture medium, and harvesting the yogurt.

It has been found that addition of small amounts of potato protein protease inhibitor, such as a potato protease inhibitor isolate ("PPII"), to a fermentation feed significantly reduces the lag time of the fermentation, which has economic benefits in the production of yogurt. The required amount of potato protein is low enough not to affect the taste of the yogurt, and the lag time reduction occurs bath in batch- and in semi-continuous processes. Lag time reduction, in the context of the present invention, can also be called "stimulating activity" (SA).

Also, the present invention can be applied in a wide pH- and temperature range.

The present method is directed to fermentation processes for the production of yogurt. Preferably, the present invention is applied in a fermentation process in which the growth of the microorganism is peptide-limited. Peptides, for the scope of the present invention, are small protein fragments, consisting of 5-30 amino acids; such fragments are also called "nutritious peptides".

A peptide-limited fermentation is a fermentation where the concentration of free nutritious peptides is limited but where other necessary nutrients, like (trace) minerals, carbohydrates and proteins, are freely available. This limitation of peptides occurs when the rate of degradation of nutritious peptides by proteases/peptidases towards amino acids is higher than the rate of formation of nutritious peptides from protein. It can be tested whether a fermentation is peptide-limited by observing the effect of addition of small amounts of peptides on growth and lag time. When addition of nutritious peptides does not result in a substantially faster fermentation, then the fermentation is not peptide-limited. When addition of nutritious peptides does result in a faster fermentation, then the fermentation can be called peptide-limited.

This means that the fermentation rate is dependent on the concentration of available nutritious peptides. In case of a peptide-limited fermentation, there are insufficient nutritious peptides to sustain or to adapt towards exponential growth of the microorganism. This leads to an increase in lag time.

In the method of the present invention, addition of a relatively small amount of potato protein protease inhibitor is found to reduce the lag time, in particular for peptide-limited fermentations, and in particular where sufficient proteins are available.

It is unexpected that in particular in methods involving a peptide-limited fermentation the lag time is reduced. It is well-known that an important factor in determining the lag-time of a fermentation is the degradation of proteins in the medium to small nutritious peptides of 5-30 amino acids. This conversion is effected by a wide variety of proteases. A well-known function of protease inhibitors is to inhibit proteases, effectively inhibiting the proteases which are responsible for the degradation of proteins to nutritious peptides. As such, it would be expected that addition of protease inhibitors, of whatever source, would result in an increased lag time due to slower enzymatic degradation of proteins and an associated slower formation of nutritious peptides. However, it is now found that in fact the opposite occurs, and addition of potato protein protease inhibitors results in a reduced, rather than an increased, lag time.

The lag time, in the present context, is defined as the time duration required for the microorganism to adapt to the new environment, the culture medium. It is the time duration required for the lag phase.

A yogurt fermentation process can be monitored via various suitable metabolic output parameters. For instance, the pH might be a suitable metabolic out-put parameter. Alternatively, the optical density (OD at 600 nm, OD600) might provide a suitable output parameter, to provide a quantification of the amount of microorganisms present. However, the skilled person can come up with numerous ways to determine the progression of a fermentation, and determine the time required for the lag phase in yogurt production.

Fermentation generally progresses through an S-shaped curve in output parameters such as optical density or pH, as is well-known in the art. In the present invention, the time to reach the half-way point in the exponential curve is found by calculating the inflection point in the smoothed S-curve from its second derivative. Alternatively, when using pH as an indicator of metabolic progress, one takes a pH-value half way the exponential curve and records the time until this pH is reached. In yogurt production any pH between pH 5.0 and pH 5.5 can be used, provided that this value is applied consistently to allow appropriate comparison. The reduction in lag time can be determined by comparing the lag time of a fermentation without added potato protein protease inhibitor with the same fermentation wherein an appropriate quantity of potato protein protease inhibitor is added. The absolute lag time reduction is generally quantified as hours of reduction, while the relative lag time reduction is quantified as "%".

Native potato proteins can tentatively be divided into three classes (i) the patatin family, a highly homologous acidic 43 kDa glycoproteins (40-50 wt. % of the potato proteins), (ii) basic 5-25 kDa protease inhibitors (potato protein protease inhibitors), which, when isolated, are termed potato protease inhibitor isolate or "PRII"; 30-40 wt. % of the potato proteins) and (iii) other proteins mostly high molecular weight proteins (10-20 wt. % of the potato proteins) (Pots et al., J. Sci. Food. Agric. 1999, 79, 1557-1564).

PPII can be divided into different groups based on their molecular weight. The different groups of protease inhibitors are identified as protease inhibitor I (molecular weight of about 39 kDa), carboxypeptidase inhibitor (molecular weight of about 4 100 Da), protease inhibitors IIa and IIb (molecular weight of about 20.7 kDa), and protease inhibitor A5 (molecular weight of about 26 kDa). The ratio of these different groups of protease inhibitors in the total potato protein depends on the potato variety.

For the scope of the present invention, a potato protein protease inhibitor comprises any potato protein protease inhibitor, or any mixture of different potato proteins, which includes one or more potato protein protease inhibitors, or groups of inhibitors, as defined above. A potato protease inhibitor isolate (PPII) is an isolate comprising a potato protein protease inhibitor. PPII can be obtained in any known way, such as by e.g. precipitation, heat fractionation at 60-80° C., membrane separation, precipitation with ammonium sulphate or saturated fatty acids or other components, filtration techniques such as ultrafiltration or gel filtration.

Preferably, PPII is used in the present invention. This may be obtained as described in WO2008/069650, the contents of which are incorporated herein by reference, where an elaborate description of the isolation of protease inhibitors from potato fruit juice (PFJ) or potato fruit water (PFW) is described.

That process entails subjecting potato fruit juice to a flocculation by a divalent metal cation at a pH of 7-9, and centrifuging the flocculated potato fruit juice, thereby forming a supernatant. Subsequently, the supernatant is subjected to expanded bed adsorption chromatography operated at a pH of less than 11, and a temperature of 5-35° C. using an adsorbent capable of binding potato protein, thereby adsorbing the native potato protein to the adsorbent. Column materials that bind certain amounts of native potato proteins include mixed-mode adsorbentia such as for example Amersham Streamline™ Direct CST I (GE Healthcare), Fastline adsorbentia (Upfront Chromatography A/S), macroporous adsorbentia such as Amberlitem™ XAD7HP (Röhm & Haas Company) and ion exchange adsorbents. Alternatively, absorbentia comprising ligands such as disclosed in European patent application 12175944.3 are highly preferred to isolate PPII suitable for use in the present invention.

Finally, at least one native potato protein isolate is eluted from the adsorbent with an eluent. This method results among others in isolated PPII of high purity, with a minimum of denatured protein present and characterised by a stable solubility. As a result, this method results in native PPII. Native PPII is generally preferred in the method of the present invention.

The quantity of potato protein protease inhibitors can be determined by measuring the inhibitory effect against trypsin according to the method described in Spelbrink et al., The Open Food Science Journal 2011 (5) p 42-46 "Quantitative Determination Trypsin Inhibitory Activity in Complex Matrices" or in ISO 14902:2001E "Animal Feed Stuffs—Determination of soya products".

As an alternative to using potato protein protease inhibitor, such as in PPII, it is possible to use a further purified protein fraction isolated from PPII. A preferred protein fraction Is soluble at pH 8

Has a pKa<8

Has both TIA and CTIA activity, but neither activity survives heat treatment at 80° C. for 30 minutes. Nevertheless the lag time reducing capacity remains intact up to at least 90° C.

Has a molecular weight between 17.5 and 18.2 kDa.

TIA activity is determined by measuring the inhibitory effect of the protein against trypsin according to the method described in Spelbrink et al The Open Food Science Journal 2011 (5) p 42-46 "Quantitative Determination Trypsin Inhibitory Activity in Complex Matrices" or in ISO 14902: 2001E "Animal Feed Stuffs—Determination of soya products".

CTIA activity is determined by measuring the inhibitory effect of the protein against chymotrypsin. The method to be used is essentially the same as the method described for TIA, but higher enzyme doses are required to compensate for chymotrypsins lower specific activity.

An advantage of using a potato protein protease inhibitor is that the majority is very heat stable. The active fraction in the potato protein protease inhibitor isolate that accounts for the reduction in lag time retains its native state up to temperatures of 60° C., preferably 70° C., more preferably 80° C., and most preferably 90° C. for a period of at least 15 min, preferably at least 90 min. This allows the addition of potato protein protease inhibitor at different points in the fermentation process. It can be added to the medium before, after or during the addition of the starter culture, or it can be added to the starter culture itself.

Also, it may be added to a fermentation feed in processes wherein the fermentation feed is heated prior to fermentation. This is the case for instance in processes which require pasteurization or sterilization prior to fermentation, which is common in many yogurt production processes.

It is a further advantage of the present invention that potato protein protease inhibitor is functional in fermentation processes as described in very low concentrations. In particular, addition of less than 1 g/l, preferably less than 0.5 g/l, more preferably less than 0.1 g/l, even more preferably less than 0.05 g/l of potato protein protease inhibitor is sufficient to reduce the lag time in fermentation processes according to the invention. A minimum amount of at least 0.01 g/l preferably 0.005 g/l, more preferably 0.001 g/l potato protein protease inhibitor is required to reduce the lag time of fermentations according to the present invention.

Preferred concentrations of potato protein protease inhibitor are between for instance 5 g/l and 0.001 g/l, preferably between 5 g/l and 0.05 g/l, more preferably between 5 g/l and 0.01 g/l, such as between 1 g/l and 0.01 g/l. The concentration of potato protein protease inhibitor in this context is expressed as g potato protein protease inhibitor per liter culture medium.

At these concentrations, potato protein protease inhibitor confers no taste to the yogurt, which is an additional advantage. Further additionally, these low concentrations of potato protein protease inhibitor have no detectable impact on the sensory characteristics of the yogurt. However, higher concentration of potato protein protease inhibitor of more than 0.5 up to 2% improves the structure and sensory characteristic e.g. smoothness of the final yogurt product.

It is also an advantage of the present invention that potato protein protease inhibitor is functional in fermentation processes in a wide pH-range. In particular, the pH in the culture medium may be up to 6.7, preferably 8.0 more preferably up to 10.0. Also, the pH may be as low as 4 preferably as low as 3, more preferably as low as 2. The stability of potato protein protease inhibitor in a wide pH range is advantageous because it allows culture media of various pH's to be processed by fermentation. In addition, it allows yogurt fermentation to benefit from addition of potato protein protease inhibitor throughout the fermentation.

Furthermore, it is a distinct advantage of the present invention that potato protein protease inhibitor is non-allergenic. This means that it can be used in yogurt fermentation processes operated by people allergic to other proteins. Also, this means that it can be used for fermentation of yogurt, wherein the yogurt can be consumed by people with allergies without a risk of allergic shock.

In addition, it is an advantage of potato protein protease inhibitor that a solution of this protein, preferably an aqueous solution, is clear, or at least substantially non-turbid, up to concentrations of at least 10 g/L, preferably 50 g/L, more preferably 250 g/L. These concentrations are preferably attained at a solution pH of 2 to 5, preferably 2-4, more preferably 2.5-3.5. Clear or substantially non-turbid solutions of potato protein protease inhibitor allow for convenient filter sterilization and attractive appearance of the yogurt.

In a comparison of potato protein protease inhibitors with protease inhibitors from other sources, it was found that egg protein protease inhibitors did not display the reduction in lag time at comparable dosage, in contrast to potato protein protease inhibitors. Also, whey protein isolates (WPI) and carboxy peptidase inhibitors (CPI) did not show a reduction in lag time at comparable dosages.

However, soy protein protease inhibitors and pea protein protease inhibitors can exhibit a reduction in lag time upon addition to a suitable culture medium, such as one comprising milk. However, higher dosages of soy protein protease inhibitors or pea protein protease inhibitors are needed, because the lag time reduction at the same dose is significantly lower for pea and soy protein than for potato protein (see FIG. 8a).

All of the presently described parameters for the use of potato protein protease inhibitors in a method of fermentation with reduced lag time also hold for pea protein and soy protein protease inhibitors, and any parameter, or combination of parameters, described for potato protein protease inhibitors is considered valid for pea protein protease inhibitors and soy protein protease inhibitors, also. Therefore plant protein protease inhibitors, such as those derived from Angiosperms (flowering plants) or culinary vegetables, preferably pea, soy or potato protein protease inhibitors, may be similarly used in a method of yogurt fermentation with reduced lag time according to the present invention.

However, not all advantages of potato protein protease inhibitors similarly apply to other plant protein protease inhibitors. In particular, soy flour does not display the heat stability of potato protein protease inhibitors. Therefore, soy flour cannot be used in a method of fermentation to reduce the lag time in which it is heated with the culture medium prior to fermentation, such as in a method which includes a pasteurization or (filter/heat) sterilization step prior to fermentation. This is an advantage of potato protein protease inhibitors over soy protein protease inhibitors in soy flour.

Isolated pea and soy protein protease inhibitors display heat stability. When performing a fermentation according to the present invention with PPII, the lag time reduction after a heat treatment step is more or less the same as the lag time reduction observed without a prior heat treatment step. This is similar for isolated pea and soy protein, which activity is more or less the same with or without a prior heat treatment step, even though the lag time reduction of pea and soy protein in absolute terms is lower than for potato protein, as described above.

A further drawback of using pea or soy protein, relative to using potato protein, is that the lower activity in lag time reduction makes that higher concentrations are needed. This leads to an increased risk that the added protein conveys taste to the yogurt, which is a drawback.

In addition, both pea and soy protein protease inhibitors are allergenic proteins, which are cumbersome to apply in general food production processes due to enhanced risk and regulation relative to potato protein.

Therefore, potato protein protease inhibitors are superior in terms of heat stability, lag time reduction and general industrial applicability in fermentation over protease inhibitors from other sources. However, any plant protein protease inhibitors, such as those derived from Angiosperms (flowering plants) or culinary vegetables, preferably pea, soy or potato protein protease inhibitors, displays the reduction in lag time upon addition to a yogurt fermentation feed.

All the above advantages of potato protein protease inhibitor also apply to PPII, where it is used as potato protein protease inhibitor.

In particular, in the case of PPII, it is an advantage that PPII comprises a high amount of heat-stable fraction, which similarly allows the use of potato protein protease inhibitor according to the present invention in processes wherein the fermentation feed is heated prior to fermentation. PPII generally comprises between 20 and 80 wt. %, preferably between 40 and 60 wt. % of heat-stable potato protein protease inhibitors, so that addition of only low amounts of PPII results in a reduced lag-time. Also in this case, no taste is conferred to the final product.

Alternatively, the heat stable fraction of may be isolated from PPII prior to application of the potato protein protease inhibitor in a fermentation process. This can be done by thermal precipitation and subsequent filtering of the non-heat stable proteins in PPII, whereupon the heat-stable fraction of PPII is isolated as a solution of heat-stable potato protein protease inhibitor, which may optionally be isolated as a powder, for instance by freeze-drying. Alternatively, heat-stable potato protein protease inhibitor can be obtained by fractionation of PPII, such as by ion exchange chromatography by eluting at a pH corresponding to the majority of heat stable protease inhibitors, and also by adsorption processes, membrane filtration, gel filtration or selective precipitation.

Microorganisms for the method for preparing yogurt by fermentation are those which are suitable for producing yogurt. Suitable microorganisms comprise for example microorganisms from *Lactobacillus, Lactococcus, Streptococcus, Leuconostoc* and *Bifidobacterium*.

A fermentation starter culture, in the context of the present invention, is a culture comprising one or more microorganisms appropriate to obtain yogurt. A starter culture may comprise a single microorganism type, or it may comprise two or more microorganisms. Suitable starter cultures comprise the organisms present in Kefir such as lactic acid bacteria and yeasts, as well as *Lactobacillus, Lactococcus, Bifidobacterium breve, Streptococcus thermophilus, Leu-* conostoc mesenteroides, Lactococcus lactis, Lactococcus cremoris, e.g. mixtures of Lactococcus diacetylactis and Leuconostoc cremoris.

The culture medium must be appropriate for yogurt fermentation. A suitable culture medium comprises milk, such as for example cow's milk, goat's milk, sheep's milk, yak milk, mare's milk, reindeer milk, moose milk, buffalo milk, donkey milk and/or camel milk, preferably cow's milk.

The culture conditions during fermentation can be those known for fermentation of yogurt. Culture conditions may be aerobic or anaerobic, and if aerobic, may involve, low, regular or high aeration. Culturing can be solid state or liquid state culturing, and may be done on whatever scale, in batch or semi-continuous processing methods. The oxygen levels may vary from absent (anaerobic fermentation) to present (aerobic fermentation). The processing may be both stirred as well as static.

The temperature during fermentation may vary from −10° C. to +60° C., preferably from 13-45° C. Preferably, the temperature remains constant. The may vary from pH 2-10, preferably 4-6.7. The culturing time is highly variable and depends on the type of culture. The skilled person is well aware of suitable culturing times for yogurt. Accordingly, culturing times may vary between 0.5 hr and 10 years or more, or any time in between.

Addition of the potato protein protease inhibitor may occur at any time before the fermentation. Such adding can be done by combining the potato protein protease inhibitor with the culture medium as a filtered or pasteurized protein concentrated solution, and then adding the starter culture, or alternatively, by combining the starter culture with the native potato protein and combining this mixture with the culture medium. Alternatively, all components may be added separately, or in combination with further constituents of the culture medium, as the case may be. Such further constituents of the culture medium may include for instance carbohydrates, trace minerals, bulk minerals, proteins, peptides.

In a much preferred embodiment, the potato protein protease inhibitor can be added to the culture medium prior to a heating step. This is advantageous when the culture medium is to be heated, such as for pasteurization or sterilization, prior to addition of the starter culture. Due to the advantageous heat stability of potato protein protease inhibitor, potato protein protease inhibitor retains its native state even after such heating, so that its natural biochemical function remains and the lag time of the fermentation is reduced even after heating.

Addition of potato protein protease inhibitor, preferably in native state, has the effect of reducing the lag time of the fermentation. The lag time is reduced significantly, depending on the culture and the medium, such as by at least 10%, preferably at least 25%, more preferably at least 50%, more preferably at least 60%, and most preferably at least 90%, relative to the same fermenting method wherein no potato protein protease inhibitor is added.

Harvesting the yogurt may take any form known in the art for the isolation of yogurt after fermentation. In particular, a yogurt may be obtained by monitoring a suitable metabolic out-put parameter (such as pH or optical density), determining the end point of fermentation, and isolating the yogurt.

The invention will now be further elucidated by the following, non-limiting examples.

EXAMPLES

Example 1: Production of Yogurt

PPI-isolate is a potato protease inhibitor isolate, and can be abbreviated PPII. PPI-isolate has been added to the fermentation mixture at 2 different points in the process, namely 1) to the milk before pasteurisation and 2) to the milk after pasteurisation together with the starterculture. A third option is adding the PPII during the production of the starter culture, keeping in mind the final concentration of the PHII in the milk/yogurt.

The process is schematically given in FIG. 1. Fresh yogurt was prepared by pasteurization of the milk (unless stated otherwise 30 min, 80° C.) and cooling to 40-42° C. The possible process steps where the PPI-isolate can be added are shown in the figure. It was noted that when PPII was added in higher dosages the pH decreases. Therefore, it is advised to readjust the pH to pH 6.7 with e.g. NaOH, as a lower pH would affect the texture of the yogurt.

For preparing the yogurts the milk was inoculated with either 2% (w/w) commercial yogurt, or the advised amount of starter culture from f.i. CSK Food Enrichment B.V. (1 unit/10 L≈0.02% (m/m)) or from DSM, Delvo-Yog® CY (5 units/1000 L), and fermented for 4-7 h to reach a pH of 4.5. The used standard yogurt culture, CESKA®-Star Y200, contains the lactic acid bacteria Streptococcus thermophilus and Lactobacillus bulgaricus. The experiments were done on small scale (25-50 mL) and immediately after inoculation the samples were incubated in a water bath at 40-42° C.

All experiments were stopped as soon as pH reaches pH 4.5. The pH was automatically recorded during fermentation at 2-15 minute intervals (WTW, Germany).

Figure 2:
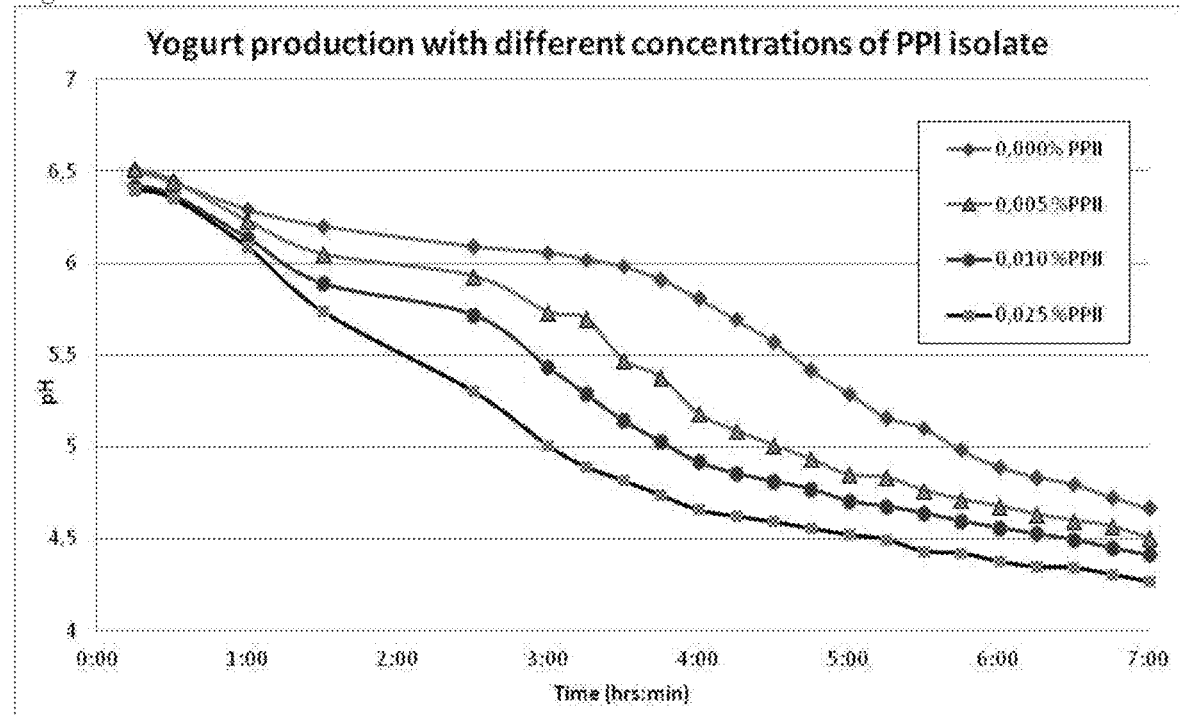
FIG. 2: Time-dependent reduction during yogurt manufacture at varying concentration of PPII; a higher concentration PPII results in faster pH reduction.
Figure 3:
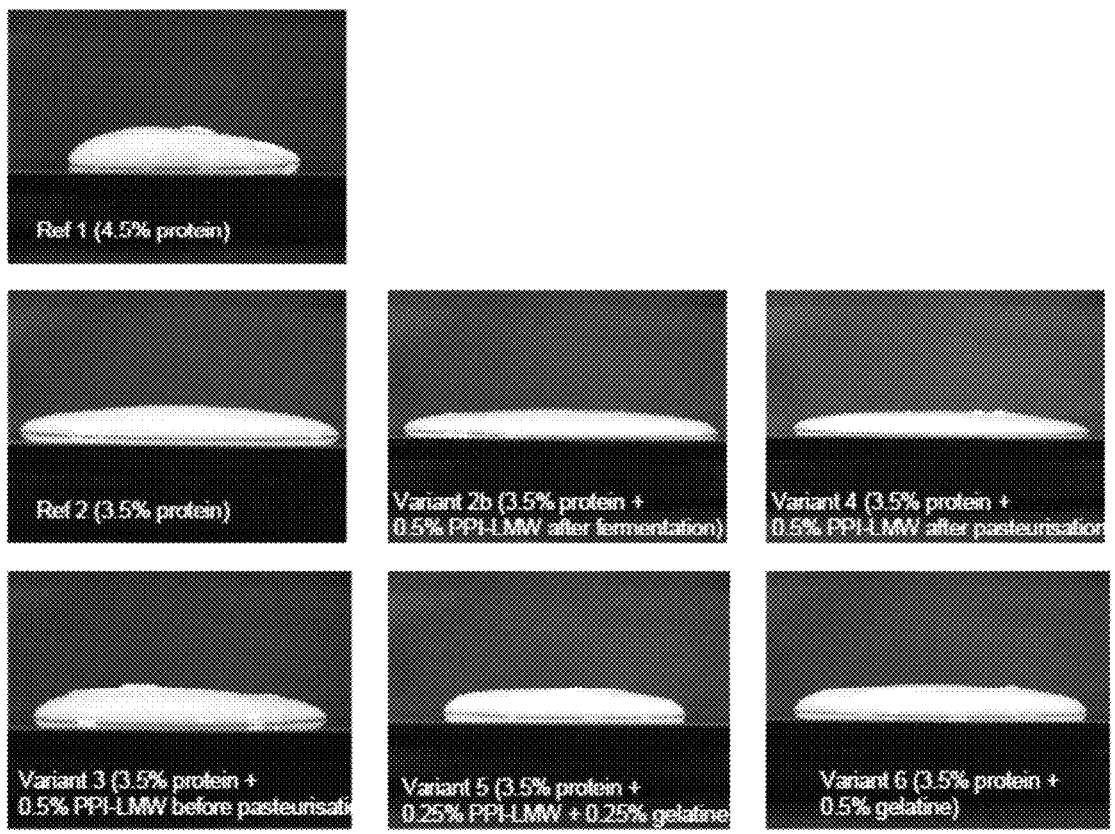
FIG. 3: Photographs of yogurt products

An acidification curve during fermentation with a 2% yogurt dosage as inoculums is shown in FIG. 2. The reference yogurt with 0% PPII reached pH 5.0 after 5:45 h. The yogurt with 0.025% PPII reached pH 5.0 after 3 h. The fermentation time for the yogurts made with PPII was significantly shorter compared to that for the blank yogurt. The time reduction that can be reached depends to a large extend on the viability and growth phase of the inoculums. When the cells in the inoculums are in the stationary phase (f.i. when 2% yogurt is used as inocula), the lag time of the blank/reference yogurt is very large and the possible time reduction is therefore very high.

Example 2: PPII Dependency of Reduction of Lag Time in Yogurt Production

Yogurts were prepared according to Example 1, with different PPII dosages, ranging from 0.005% to 0.025% (w/w). The achieved time reduction by addition of PPII was plotted against the dosed concentration of PPII. The time that the fermentation needed to reach pH 5.0 was used to compare the effect on the lag time of various doses of PPII. With increasing amounts of potato protein protease inhibitor isolate the fermentation time decreased significantly, as is shown in FIG. 2.

Example 3: Heat Stability of Potato Protein Protease Inhibitor Isolate

Figure 4:
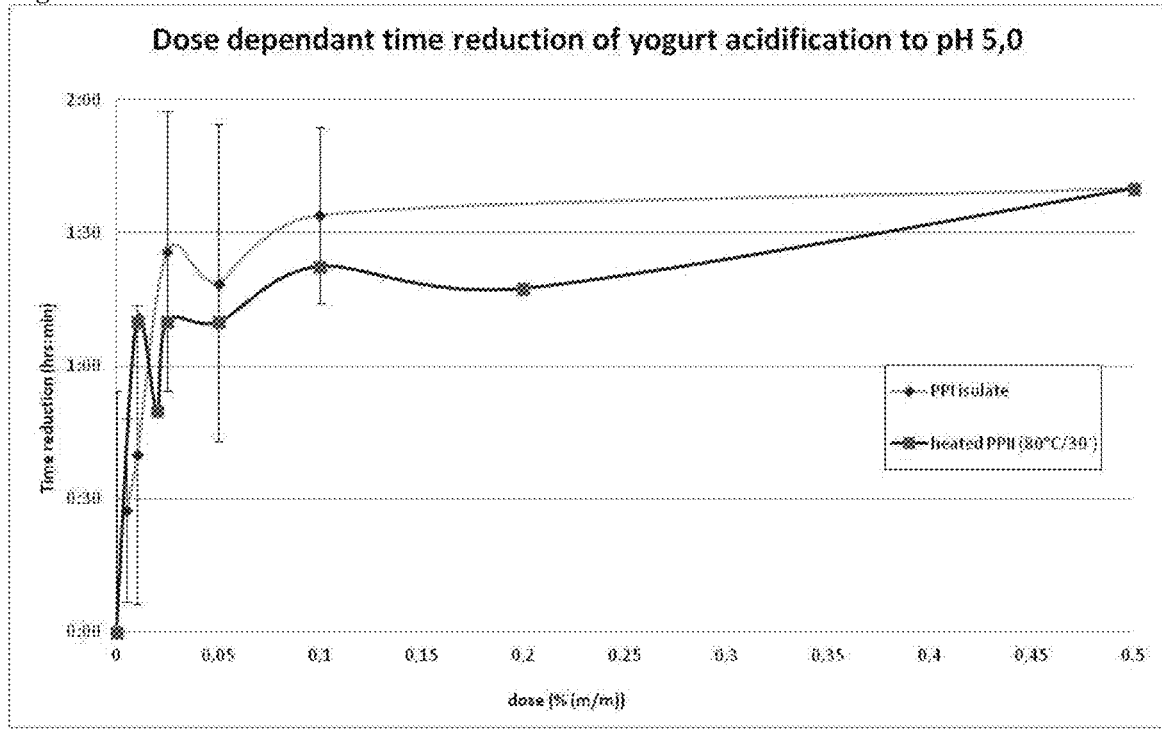
FIG. 4: Time reduction in attaining pH 5 during yogurt manufacture using standard culture and 3.5% milk protein, at varying concentrations PPII, with and without a pre-fermentation heat treatment.
Figure 5:
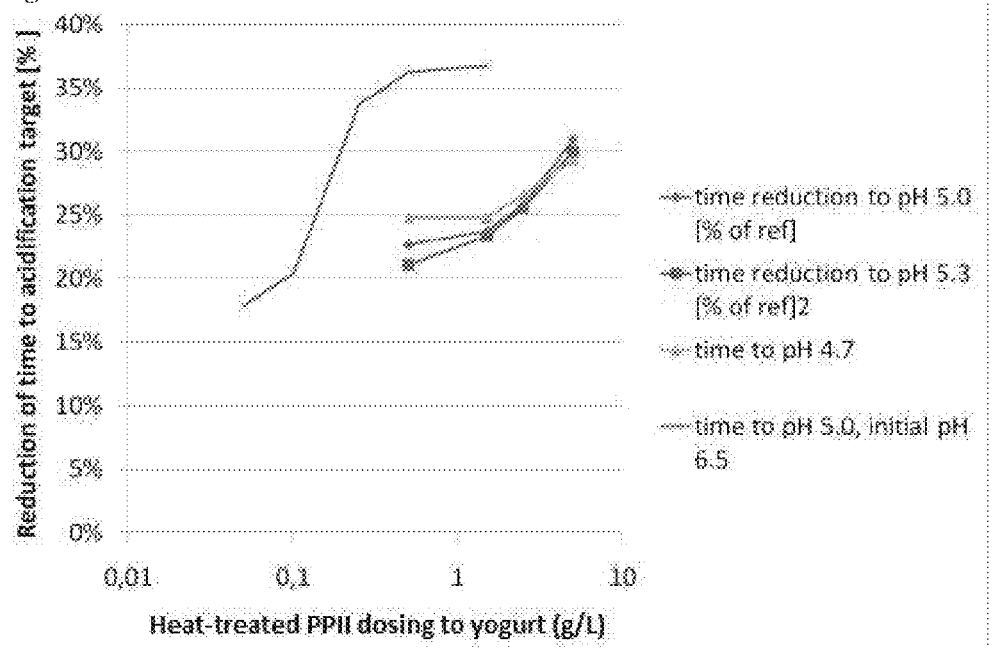
FIG. 5: The growth curve graph of fermentation time to pH 5.0, 5.3 and 4.7 of yogurt made using standard culture and at varying concentration PPII, added to 3.5% milk protein during yogurt manufacture.
Figure 6:
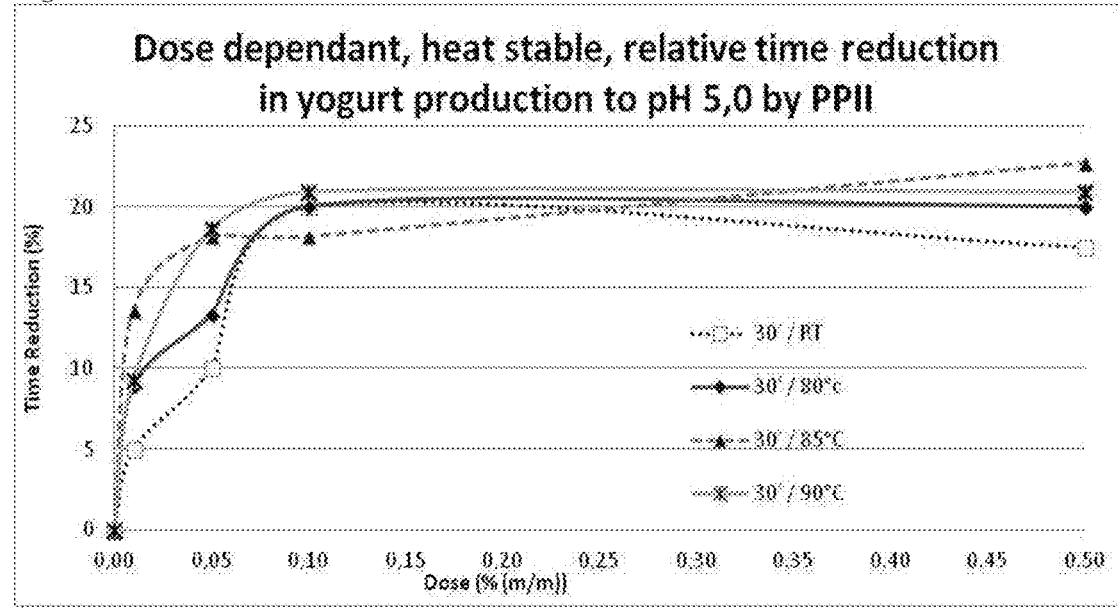
FIG. 6: Time reduction in achieving target pH 5.0 for fermentations in the presence of varying concentrations PPII with and without pre-fermentation heat treatment at different temperatures, using standard culture added to 3.5% milk protein.

Addition of PHI before or after pasteurisation both resulted in comparable dose dependent time reduction curves (FIGS. 4 and 6). Yogurts were prepared using a predefined starter culture, as described in the previous two examples. The PPII was added to the milk prior to pasteurisation. The milk-PPII premix was not pasteurized (room temperature, RT), or pasteurised for 30 minutes at 3 different temperatures, 80° C., 85° C. and 90° C. The obtained (absolute and relative) time reductions for all samples were dependent on the dosage of PPII and no significant difference was observed between the different heat treatments.

Optimal PPII dosage in this experiment was found to be 0.1% PPII and this resulted in a significant relative time reduction (≈20%).

Example 4: Potato Protein Proteas Inhibitors for use in the Present Invention can be Native A 30 g/L azocasein (SigmaAldrich, A2765) stock solution was prepared by dissolving the protein in 100 mM pH 5.0 Citrate-buffer containing 5 mM of $CaCl_2$ (SigmaAldrich, C3881) at 50° C. and cooling back to 37° C. Lyophilized fungal lysates containing protease activity were dissolved in 1 mM HCl solution. PPII was dissolved in pH 3.0 acetate solution.

Figure 7:
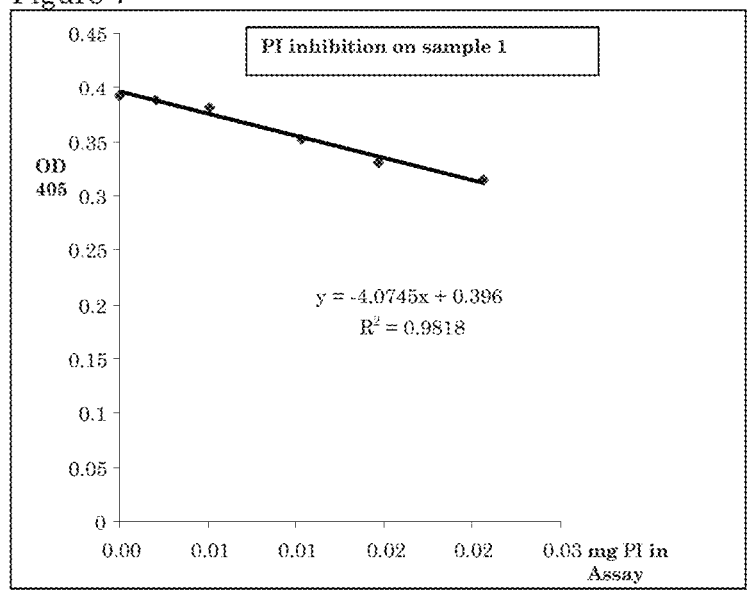
FIG. 7: Protease inhibition by Solanic PHI protein on freeze dried fraction of *Arthomyees ramous* Peroxidase (ArP) production by modified *Aspergillus awamori*.

From a PPII solution a series of dilutions was prepared in such a way as to cause a ~50% loss of signal upon incubation for the highest sample concentration. From each dilution, 125 µL was mixed with 25 µL of fungal protease solution in an eppendorf cup, or with 25 µL of demineralised water as a control. Positive and negative controls for the proteolytic reaction used 125 µL of demineralised water rather than sample material. To these mixtures 225 µL of warm azocasein were added, followed by a 30 minute incubation at 37.0° C. The reaction was then quenched by the addition of 150 µL of 15% w:v TCA solution, The order of addition of azocasein was the same as the order of addition of TCA to ensure equal incubation times for all samples see FIG. 7)

Non-hydrolysed azocasein and other insolubles were removed by centrifugation at 15,000 g at 40 C for 10 minutes in a Heraeus Multifuge 1S-R using a Thermo Scientific rotor. 100 µL of the supernatant were transferred to a microtiter plate by careful pipetting and supplemented with 100 µL of 1.5 M NaOH solution. The plate was then analysed for absorbance at 450 nm on a BioRad Model 680 microplate reader.

The absorbencies were plotted against the amount of sample material in the plate. The slope of the resulting line was obtained via linear regression using the least squares method and indicates the amount of absorbance lost per quantity of sample material. The positive control, in the absence of sample, indicates the maximum absorbance caused by the known quantity of protease solution. Hence, by dividing the slope by the positive controls' absorbance, the trypsin inhibitory activity expressed as the amount of protease inhibited per amount of sample material was obtained.

It follows that the PHI used in the present experiments can be native.

Example 5: Comparison with Protease Inhibitor Proteins from Other Sources than Potato Protease inhibitors from two plant sources, pea and soy, were tested for their ability to reduce the lag time in yogurt fermentation because these proteins are most readily available for large-scale commercial processing. Furthermore, egg protein was tested since this represents a major source of animal-derived dietary protease inhibitors.

Figure 8A:
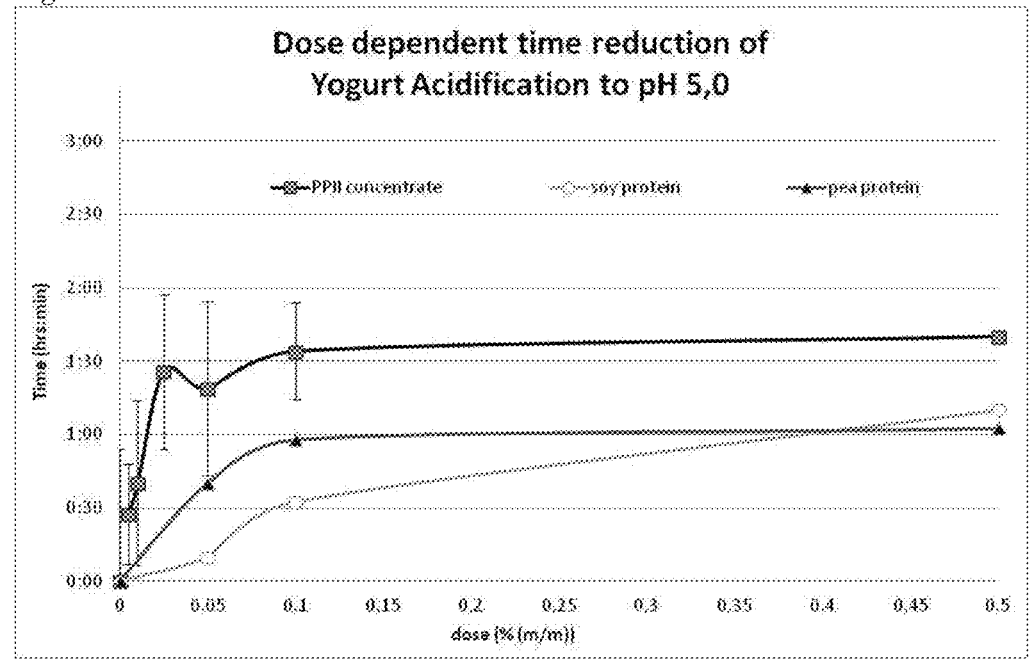
FIG. 8a: Dose dependent time reduction in yogurt production time by potato protease inhibitor isolate, soy protease inhibitors and pea protease inhibitors.

Two types of pea protein were tested, Pisane® C9 and Pisane® F9 from Cosucra. Also, raw soy flour (SigmaAldrich) and soy protein (Profam, ADM), as well as egg protein and PPII were used. FIG. 8a shows the dose dependent time reductions for both soy and pea protein, in fermentations using CESKA®-Star Y200 of CSK Food Enrichment B.V., where the proteins do not undergo a heat treatment prior to fermentation. Egg protein showed only minor lag time reduction (not shown). Raw soy flour showed a higher lag time reduction than pea protein, but dosage was done on protein end concentration, which means that very high dosages of soy flour were required. The lag time reduction using soy protein is, however, distinctly less than the lag time reduction using potato protein protease inhibitor, as exemplified by the use of PPII.

For pea protein, both Pisane® C9 and Pisane® F9 were used. Both types gave the same lag time reduction, which is much less than the lag time reduction observed for potato protein protease inhibitor, as exemplified by the use of PPII.

PPII shows to have the highest lag time reduction, and is superior to both pea and soy protein for yogurt fermentation, resulting in a shorter fermentation time, as can be seen from FIG. 8a.

Figure 8B:
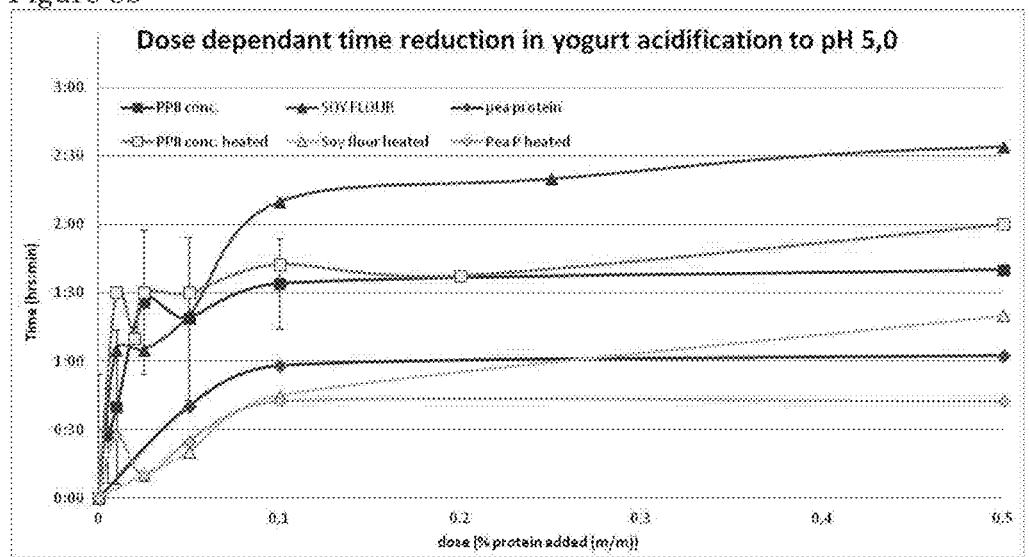
FIG. 8b: Dose dependent time reduction in attaining pH 5 during yogurt manufacture using standard starter culture and using PPII, pea protein, and soy flour with and without pre-fermentation heat treatment (80° C., 30 minutes).

Potato protein, isolated soy protein and isolated pea protein showed to be heat resistant. No significant change in dose dependent yogurt lag time reduction was observed for these proteins between before and after heat treatment (80° C. for 30 minutes). The lag time reduction of raw soy flour does, however, not survive a heat treatment (FIG. 8b).

Example 6: Lag Time Reduction in Various Fermentation Systems, First Example

To validate the lag-time reduction of PPII in different yogurt systems, different commercial starter cultures were tested. The starter cultures were chosen such that maximum variation in orders of viscosity and postacidification of the final yogurt could be evaluated. The tested starter cultures were Ceska®-star yoghurt cultures Y200, Y700, Y900, Y104 and Y508 (various mixtures of St. thermophilus and Lb. delbrueckii subsp. bulgaricus), and B193 (mixture of St. thermophilus, Lb. delbrueckii subsp. bulgaricus, Lb. acidophihis and Bifidobacteria), of CSK Food Enrichment B.V.

Figure 9:
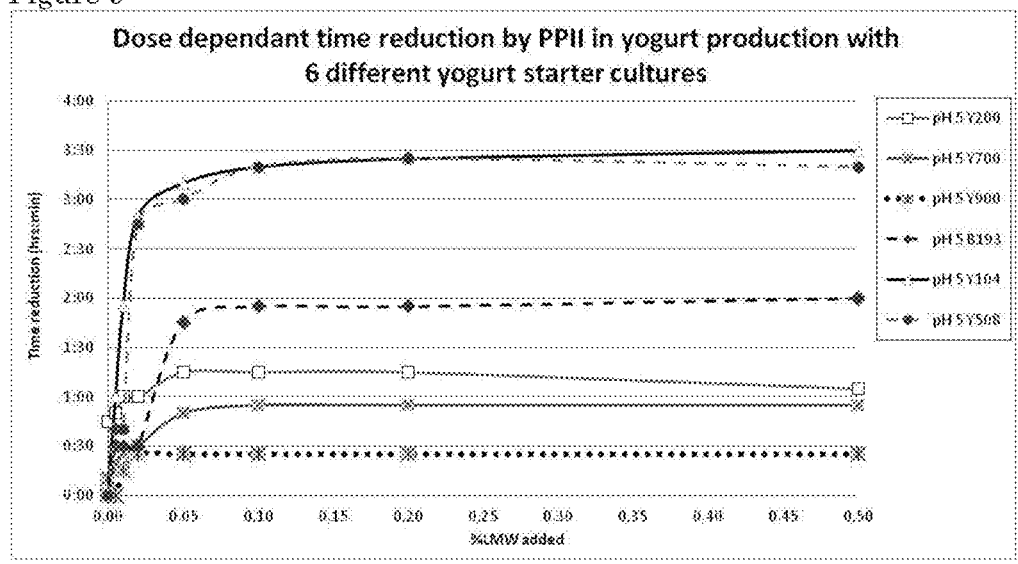
FIG. 9: Dose-dependent time reduction in yogurt manufacture to pH 5 using six different yogurt starting cultures.

Of the 6 starter cultures tested, all 6 displayed a significant lag time reduction upon addition of PPII at 0.05%-0.20% PPII dosage (FIG. 9a), resulting in a reduced yogurt production time.

Example 7: Determination of Whether a Fermentation System is Peptide-Limited

A dose response test can be performed to evaluate whether a system is peptide-limited. The principle is shown here in a model system, in which the concentration of available peptides during fermentation is varied. In a yogurt fermentation system, the peptide concentration can be similarly varied to determine whether the yogurt fermentation is peptide-limited.

The media used in this test are labelled medium A-H, and the starter culture is according to example 1. Fermentation progress was monitored by the optical density at 600 nm (OD600).

All media A-H were prepared by adding to 1000 ml water, at pH 6.2-6.5: 20 g glucose (Merck 1.08342), 1 g tween-80 (Merck 822187), 2 g $K_2HPO_4$ (Merck 1.05104), 5 g sodium acetate (Merck (1.06267), 2 g ammonium citrate (SigmaAldrich 09833), 0.2 a $MgSO_4$-$7H_2O$ (SiamaAldrich. M5921) 0.05 g $MnSO_4$—$H_2O$ (SigmaAldrich M7634) and 10 g meat extract (Fluka 70164). In addition, the media contained quantities of yeast extract ("YE", Fluka 92144) and casein peptone tryptic digest ("CP", a peptide source, Fluka 70172) as shown in table 1.

TABLE 1

RECIPES FOR MEDIA A-H

| medium | yeast extract, YE [g] | Casein peptone tryptic digest, CP [g] |
|---|---|---|
| A | 0 | 0 |
| B | 0.5 (10%) | 0.1 (10%) |
| C | 1.25 (25%) | 2.5 (25%) |
| D | 2.5 (50%) | 5 (50%) |
| E | 3.75 (75%) | 7.5 (75%) |
| F | 5 (100%) | 10 (100%) |
| G | 7.5 (150%) | 15 (150%) |
| H | 10 (200%) | 20 (200%) |

Figure 10A:
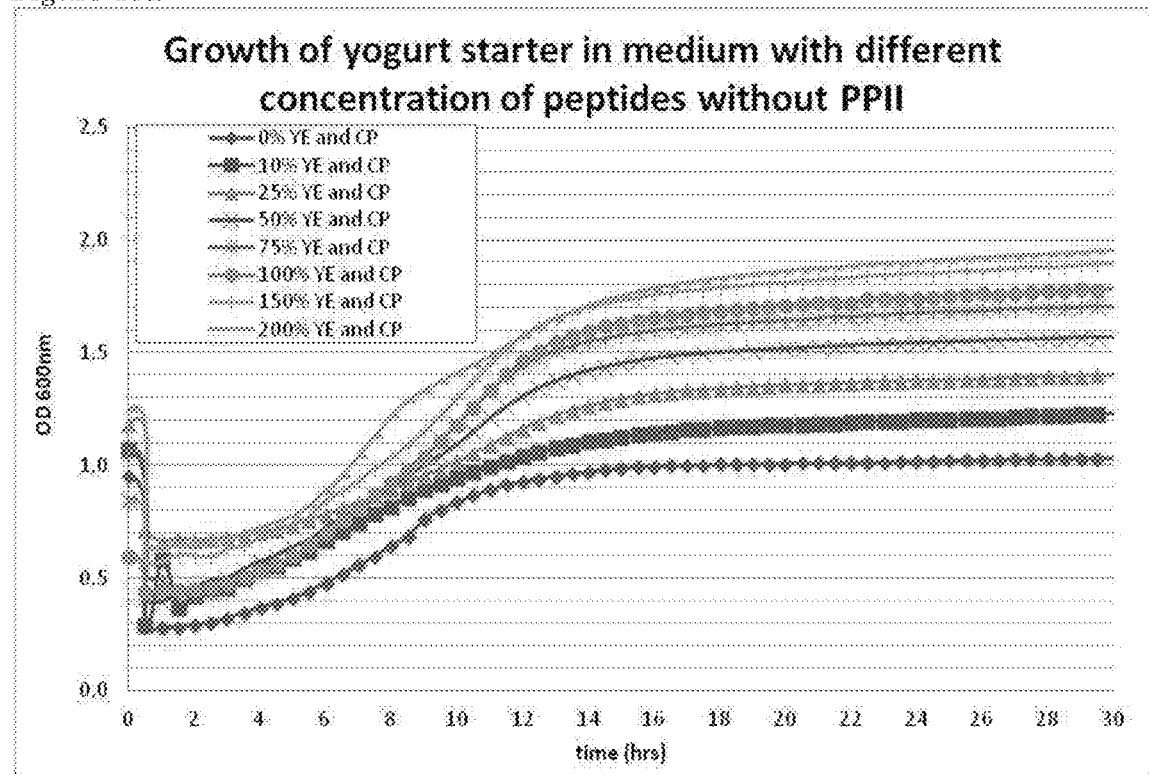
FIG. 10a: Microorganism growth in time, as observed through OD600, at increasing concentrations of peptides. A clear advantage in growth is observed when peptides are added to the medium. This medium does show not to be peptide limited anymore, in this specific situation, with this starter culture, at peptide concentrations above 75% of peptides.

FIG. 10a clearly shows the effect of increasing amounts of peptides on the growth of a yogurt starter culture. The recipes "E", "F", "G" and "H" showed more or less the same results, indicating no further reduction of lag time could be attained. This means that recipe "E" (75% YE and CP) is the optimal medium for this starter culture. A clear advantage in growth, with respect to the minimal medium "A", is observed for "B". The same goes for media "C" and "D". This means that in these cases the media for this starter culture were peptide limited, leading to a significant lag time reduction.

Figure 10B:
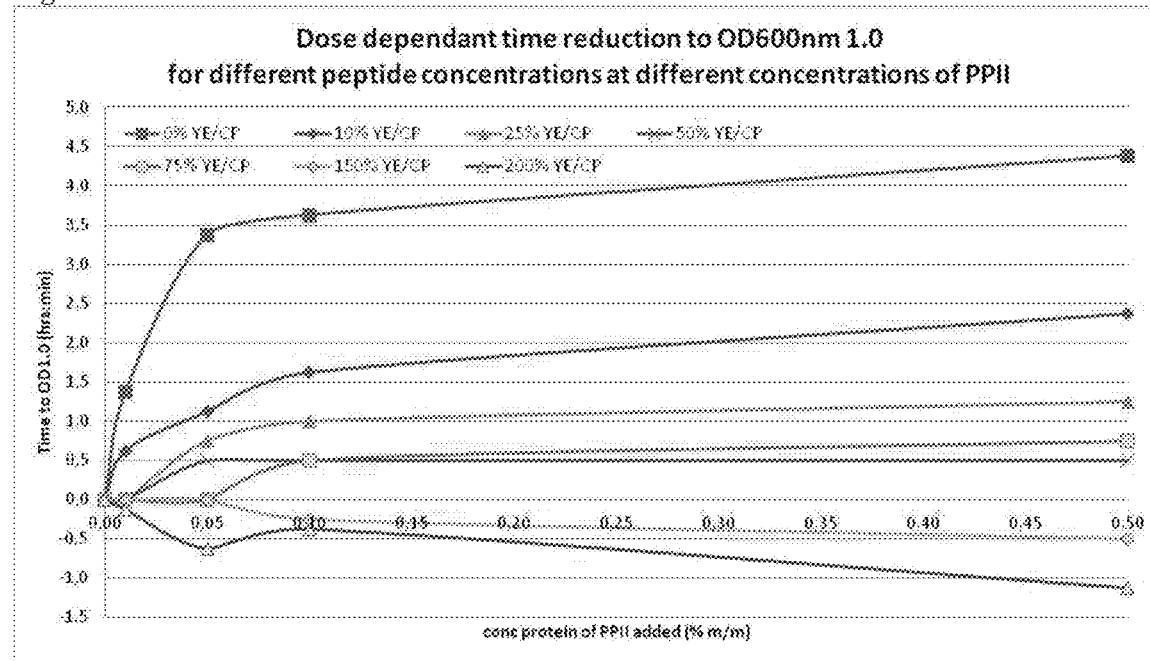
FIG. 10b: Dose dependent time reduction by evaluation of the OD600 nm for different peptide concentrations upon addition of PPII. In this specific example, in media with peptide concentrations above 75% yeast extract and casein peptone, no lag time reduction can be observed for PPII. Dose dependent time reduction for this fermentation by PPII is shown in media with peptide concentrations below 75% YE and CP.

FIG. 10b shows the effect of PPII-addition to media with different dosages of peptides (YE and CP). In this specific example, in media with peptide concentrations up to 75% yeast extract and casein peptone, lag time reduction could be observed for addition of PPII. Dose dependent time reduction by PPII for this fermentation is shown in media with peptide concentrations of 75% YE and CP, and below.

Example 8: Purification and Characterization of the Stimulating Agent

Potato protein was fractionated essentially according to the method of Pouvreau (Pouvreau 2001).

Potato protein concentrate (AVEBE) was diluted with demi water towards 1% protein solution and the pH was set to 8.0. Insolubles were removed by centrifugation at 5000 g for 10 minutes at ambient temperature. The supernatant was loaded onto a 15 by 2.6 cm column containing Source 30Q resin (GE Healthcare) and eluted using a 0 to 0.6M linear NaCl gradient. This resulted in 8 discrete protein fractions that were labeled as F1 through F8.

All fractions were tested for lag time reduction according to the method in example 1. This revealed that fractions F1 and F6 contain a strong lag time reduction, indicating that the active ingredient, a potato protein protease inhibitor, is present in these fractions. Fractions F2, F3, F4, F7 and F8 have moderate lag time reduction according to these experiments and F5 shows no lag time reduction at all. Hence, the active ingredient, a potato protein protease inhibitor, is not present in F5. The fact that the active ingredient binds to the column under the experimental conditions reveals that it is water-soluble at pH 8.0 and has an isoelectric point of 8.0 or lower.

Molecular weights of the fractions were determined on an Experion automated electrophoresis system (BioRad) according to the manufacturer's instructions under denaturing, reducing conditions. The fractions F1 and F6 that contain a strong lag time reduction share several MW bands, but only one of these is absent in the fraction F5: a band occurring between 17.5 and 18.2 kDa (Table 2). Hence, it follows that the presence of this band is indicative of strong lag time reduction.

TABLE 2

| Fraction | lag time reduction at a 0.01% dose (minutes) | Protein band present | | |
|---|---|---|---|---|
| | | 9.5 kDa | 17.5-18.2 kDa | 30 kDa |
| F1 | 60 | x | x | x |
| F2 | 5 | | | |
| F3 | 20 | | | |
| F4 | 5 | | | |
| F5 | 0 | x | | x |
| F6 | 35 | x | x | x |
| F7 | 5 | | | |
| F8 | 15 | | | |

Determination of the protease inhibitory activity according to the method specified revealed that protein fractions F1 and F6 contains both trypsin and chymotrypsin inhibitory activity, but neither activity survived a thermal treatment at 80° C. for 30 minutes. Nevertheless, lag time reduction remains intact up to at least 90° C. as shown in example 3. This demonstrates that neither TIA nor CTIA is an absolute requirement for the lag time reduction.

The invention claimed is:

1. A method for preparing yogurt wherein fermentation lag time is reduced, comprising the steps of:
   providing a fermentation starter culture comprising a microorganism selected from the group consisting of Lactobacillus, Streptococcus, Bifidobacterium and mixtures thereof in a suitable culture medium,
   adding a potato protease inhibitor to the culture medium to reduce fermentation lag time, wherein the potato protease inhibitor is present in the culture medium in a concentration of 0.001-5 g/l, wherein growth of the microorganism is peptide-limited,
   next culturing the microorganism in the culture medium derived from milk at a pH in the range of 4.5 to 6.7 at a temperature of 13° C. to 45° C., and
   harvesting the yogurt.

2. A method for preparing yogurt wherein fermentation lag time is reduced, comprising the steps of:
   providing a fermentation starter culture comprising a microorganism selected from the group consisting of Lactobacillus, Streptococcus, Bifidobacterium and mixtures thereof in a suitable culture medium,
   adding a plant protein protease inhibitor selected from the group consisting of soy and pea protease inhibitor to the culture medium to reduce fermentation lag time, wherein the protein protease inhibitor is present in the culture medium in a concentration of 0.001-5 g/l, wherein growth of the microorganism is peptide-limited,
   next culturing the microorganism in the culture medium derived from milk at a pH in the range of 4.5 to 6.7 at a temperature of 13° C. to 45° C., and
   harvesting the yogurt.

* * * * *